United States Patent [19]

Adler-Golden et al.

[11] Patent Number: 4,766,318
[45] Date of Patent: Aug. 23, 1988

[54] SPARK DISCHARGE TRACE ELEMENT DETECTION SYSTEM

[75] Inventors: Steven Adler-Golden, Newtonville; Lawrence S. Bernstein, Bedford; Fritz Bien, Concord, all of Mass.

[73] Assignee: Spectral Sciences, Inc., Burlington, Mass.

[21] Appl. No.: 866,915

[22] Filed: May 27, 1986

[51] Int. Cl.$^4$ ............................................. H01J 47/10
[52] U.S. Cl. ................................ 250/385.2; 250/374; 356/313
[58] Field of Search .............. 250/385 SC, 385.1, 374; 356/313

[56] References Cited

U.S. PATENT DOCUMENTS

| | | | |
|---|---|---|---|
| 3,653,766 | 4/1972 | Walters et al. | 356/313 |
| 3,749,975 | 7/1973 | Walters | 356/313 |
| 3,815,995 | 6/1974 | Walters et al. | 356/313 |
| 3,987,305 | 10/1976 | Gilbert | 250/374 |
| 4,055,783 | 10/1977 | Walters et al. | 315/208 |
| 4,060,708 | 11/1977 | Walters | 250/425 |
| 4,074,936 | 2/1978 | Grisar et al. | 356/313 |
| 4,076,420 | 2/1978 | De Maeyer et al. | 356/313 |
| 4,255,051 | 3/1981 | Imamura | 356/313 |
| 4,393,327 | 7/1983 | Walters et al. | 356/313 |
| 4,500,786 | 2/1985 | Britten et al. | 250/385 SC |
| 4,527,064 | 7/1985 | Anderson | 250/385 SC |
| 4,723,438 | 2/1988 | Alder-Golden et al. | 356/313 |

OTHER PUBLICATIONS

Mills, J. C. et al., "Fiber Optic Expand the Range of a Direct-Reading Spark Optical Emission Spectrometer", *Applied Spectroscopy*, vol. 38, No. 3, pp. 413–416, May/Jun. 1984.

Primary Examiner—Janice A. Howell
Assistant Examiner—William F. Rauchholz
Attorney, Agent, or Firm—Joseph S. Iandiorio; Douglas E. Denninger; Brian M. Dingman

[57] ABSTRACT

A spark discharge trace element detection system is provided which includes a spark chamber including a pair of electrodes for receiving a sample of gas to be analyzed at no greater than atmospheric pressure. A voltage is provided across the electrodes for generating a spark in the sample. The intensity of the emitted radiation in at least one primary selected narrow band of the radiation is detected. Each primary band corresponds to an element to be detected in the gas. The intensity of the emission in each detected primary band is integrated during the afterglow time interval of the spark emission and a signal representative of the integrated intensity of the emission in each selected primary bond is utilized to determine the concentration of the corresponding element in the gas.

32 Claims, 6 Drawing Sheets

SPARK DISCHARGE TRACE ELEMENT DETECTION SYSTEM

This invention was made with government support under contract number DE-AC02-83ER80085 awarded by the Department of Energy. The government has certain rights in this invention.

FIELD OF INVENTION

This invention relates to a spark discharge trace element detection system and more particularly to a system which detects the presence and amount of one or more trace elements in a gas sample at no greater than atmospheric pressure by detecting a selected narrow wavelength radiation band which is emitted from a spark discharge in the low pressure gas and which corresponds to the element to be detected.

BACKGROUND OF INVENTION

A number of techniques are presently employed for detecting trace elements in gas samples. Mass spectrometers provide fairly rapid and sensitive measurements. However, such instruments are large, complex and very expensive and typically require an expert technician to operate and maintain. Liquid and gas chromatography and related electron capture techniques are somewhat less expensive although still costly and relatively reliable but, unfortunately, are quite slow. Response time is typically on the order of seconds to minutes. Where poisonous or otherwise hazardous elements are being monitored such a delay may be fatal. Another method utilizing chemically treated tape to detect phosphorous and arsenic containing compounds is also unacceptably slow, requiring up to thirty minutes to identify low concentrations of hazardous elements.

Infrared detection techniques exhibit a faster response time. However, they do not provide optimum sensitivity. Because so many elements absorb in the infrared range the elements of interest may be easily masked. Moreover, as with the mass spectrometer, infrared systems typically require considerable maintenance and a trained operator.

SUMMARY OF INVENTION

It is therefore an object of this invention to provide a spark discharge trace element detection system which provides fast and accurate detection and measurement of trace elements in a gas sample.

It is a further object of this invention to provide a spark discharge trace element detection system which is relatively inexpensive, simple and rugged and which operates reliably and continuously over extended periods without requiring significant maintenance or trained operating personnel.

It is a further object of this invention to provide a spark discharge trace element detection system which exhibits enhanced sensitivity to low concentrations of trace elements.

It is a further object of this invention to provide a spark discharge trace element detection system which maintains a continuously replenished supply of sample gas.

It is a further object of this invention to provide a spark discharge trace element detection system which operates at low (sub atmospheric) pressures.

It is a further object of this invention to provide a spark discharge trace element detection system which is effective for identifying a wide variety of trace elements in industrial, chemical, military, and environmental applications.

This invention results from the realization that the sensitivity of a spark discharge trace element detection system may be enhanced dramatically by operating at sub-atmospheric pressure because the intensity of the background radiation is greatly reduced whereas the intensity at the identifying wavelength band is quite insensitive to pressure. Thus, as the gas pressure is reduced below one atmosphere the level of background interference is reduced drastically and a signal representing the emission intensity of the trace element of concern becomes much more distinguishable.

This invention features a spark discharge trace element detection system which includes a spark chamber having a pair of electrodes for receiving a sample of gas to be analyzed at no greater than atmospheric pressure. There are means for providing a voltage across the electrodes for generating a spark in the gas sample. There are means for detecting the intensity of the emitted radiation in at least one primary selected narrow band of the emitted radiation. Each primary band corresponds to a respective element to be detected in the gas. There are means for integrating, during the afterglow time interval of the spark emission, the intensity of the emission in each detected primary wavelength band. Means are responsive to a signal representative of the integrated intensity of the emission in each selected primary wavelength band for determining the concentration of the corresponding element in the gas.

In a preferred embodiment means are provided for separating the radiation emitted from the spark discharge into its constituent wavelengths. The means for detecting sense the intensity of the emitted radiation in at least one primary selected narrow band of the constituent wavelengths. Means may also be provided for compensating the intensity of the emission in the primary wavelength band for variations not due to the variations in the proportion of the element being detected in the gas. Such means for compensating may include means for averaging a signal representative of the intensity of the emission in the primary band over a plurality of spark discharge cycles. The means for integrating and the means for averaging a signal representative of the intensity of the emission in the first primary band may be included in a boxcar averager. The means for compensating may further include means for detecting the radiation emitted from the spark discharge in the gas in a secondary selected narrow band of the constituent wavelengths which does not correspond to an element to be detected in the gas and means may be provided for combining a signal representative of the intensity of the emission in the primary band with a signal representative of the intensity in the secondary band. The means for compensating may further include means for integrating, during the afterglow time interval of the spark emission, the intensity of the radiation in the secondary band. First means responsive to the means for integrating the intensity of the emission of the primary band may be provided for averaging over a plurality of spark discharge cycles the integrated intensity of the emission in the primary band and second means, responsive to the means for integrating the intensity of the emission in the secondary band, may be provided for averaging over a plurality of spark discharge cycles the integrated intensity of emission in the secondary band. Such means for integrating the intensity and means for averaging the integrated intensity in the primary and secondary selected bands may be included in respective boxcar averagers.

The means for combining may include means, responsive to the first and second means for averaging, for comparing the averaged integrated intensity of the emitted radiation in the primary band and the averaged integrated intensity of the emitted radiation in the secondary band and providing to the means for determining an output representative of the averaged integrated intensity of the emission in the primary band. The means for combining may include means for comparing the integrated intensity of the emission in the primary band and the integrated intensity of the emission in the secondary band. Such means for combining may also include means, responsive to the means for comparing, for averaging over a plurality of spark discharge cycles the output from the means for comparing and providing an averaged output to the means for determining.

Means may be provided for sensing the pressure of the gas to be analyzed and the means for determining may be further responsive to the means for sensing the pressure for determining the proportion of the element in the gas at the sensed pressure. Means may also be provided for sensing the temperature of the gas to be analyzed and the means for determining may be further responsive to the means for sensing the temperature for determining the proportion of the element in the gas at the sensed temperature.

Conduit means may be provided for conducting radiation emitted by the spark discharge from the spark chamber to the means for detecting. Such conduit means may include fiber optics.

The means for determining may include means for calculating the proportion of the element in the gas. Alternatively, the means for determining may include means for retrieving a stored predetermined proportion of the element in the gas corresponding to a signal representative of the integrated intensity of the emission in the primary band. The means for detecting the emitted radiation in at least one primary band may include filter means for selecting the primary narrow wavelength band. The filter means may include at least one interference filter, each of which selects an associated primary wavelength band. Likewise, the means for detecting the emitted radiation in a secondary selected band may include an interference or other filter means for selecting the secondary band. Preferably, the means for detecting includes at least one detector, each detecting a single associated wavelength band.

Means, responsive to the means for determining, may be provided for indicating the proportion of element in the gas. Alarm means, responsive to the means for determining, may also be provided for indicating the presence of at least a predetermined proportion of the element in the gas.

Typically, the gas to be analyzed is maintained at a pressure of at least 0.1 atmosphere and means are provided for regulating the gas pressure in the spark chamber to remain no greater than one atmosphere. The electrodes are typically spaced apart between one millimeter and three millimeters and the voltage applied across the electrodes is typically at most 50 kilovolts. The means for determining may include a microprocessor. The primary band may include at least one wavelength from the group including 2169, 2288, 2479, 2533, 6856, 8375, and 9212 Angstroms.

DISCLOSURE OF PREFERRED EMBODIMENT

Other objects, features and advantages will occur from the following description of a preferred embodiment and the accompanying drawings, in which.

A spark discharge trace element detection system according to this invention may be accomplished using a spark chamber for receiving a sample of gas to be analyzed at no greater than atmospheric pressure. The system is particularly effective for detecting and measuring elements such as arsenic, phosphorous, chlorine, fluorine, sulfur and carbon which are contained in poisonous agents. Typically, means such as a low-pressure pump is interconnected to the spark chamber for maintaining a sample gas pressure of below one atmosphere and preferably of at least 0.1 atmosphere. The spark chamber includes a pair of electrodes preferably spaced between 1 mm and 3 mm apart. The electrodes may include thoriated tungsten welding rods or other electrode elements. A spark circuit including a transformer may be employed to provide a stepped-up voltage of, for example, 35 kV, and up to 50 kV which is applied across the electrodes to generate a spark in the low-pressure gas sample. Each spark typically has a duration on the order of tenths of a microsecond and spark pulses are provided repetitively at a frequency of, for example, 1–10 Hz. The spark causes the element being monitored in the low-pressure gas sample to emit a characteristic spectrum. The emitted radiation typically has a lifetime on the order of several microseconds. The gas sample also provides a continuous background emission which dissipates typically in less than 1 microsecond.

Means such as a dispersive grating or a prism may be provided for separating the radiation emitted from the spark discharge into its constituent wavelengths. Further spectral filtering may be done with additional filtering. At least one primary narrow band of the constituent wavelengths corresponding to a respective element to be detected in the gas is selected such as by an interference filter or other narrow bandpass filter and detector means such as a photomultiplier or photodetector are provided for sensing each primary selected narrow band. Typically, one filter and one detector are assigned to a single narrow wavelength band.

Alternatively, a commercial optical multichannel analyzer or other comparable device may be employed for dispersing and detecting the multiple selected narrow wavelength bands. In the detection of the following elements the narrow primary wavelength bands selected include the wavelengths indicated.

| Element | Wavelength (Angstroms) |
| --- | --- |
| Arsenic | 2288 |
| Phosphorus | 2533 |
| Chlorine | 8375 |
| Fluorine | 6856 |
| Sulfur | 2169 & 9212 |
| Carbon | 2479 |

In alternative embodiments the emitted radiation need not be separated into its constituent wavelengths. Instead, at least one primary narrow band of radiation may be selected such as by a monochrometer.

A signal representative of the detected intensity is integrated during the afterglow time interval of the spark emission (starting 1 or 2 microseconds after the spark discharge). The integrated intensity signal is then further processed to determine the presence and concentration of the element or elements of interest.

To maintain consistent intensity measurements means may be provided for normalizing or otherwise compensating the intensity of the radiation emitted in the primary band to correct for errors resulting, for example, from fluctuations in spark intensity, over successive discharges. To perform such compensation means are provided for averaging a signal representative of the intensity of the emission spectra in the primary band over a plurality of spark discharge cycles. Such means for averaging may be combined with the means for integrating in a boxcar averager. Alternatively, an entirely distinct pulse averager may be used. Erroneous signals may also be accounted for using a secondary optical band. To accomplish this, radiation emitted from the spark discharge in a secondary selected narrow band of the constituent wavelengths which does not correspond to an element to be detected in the gas is also detected. For example, the secondary band typically corresponds to a continuum or line emission of carrier gas. Respective intensity signals representative of the radiation emitted in the primary and secondary bands are then integrated during the afterglow time interval of the spark emission. The integrated signal from the secondary band is compared or otherwise combined with that of the primary band through division, subtraction or otherwise to provide a compensated signal representative of the intensity of the emission in the primary band. This signal, which is pulsed, is then averaged such as by a low pass filter over many sparks. Alternatively, each of the intensity signals is integrated and averaged in respective boxcar averagers which provide signals representative of the intensities in the primary and secondary bands to a comparator, where they are combined.

In either case a compensated signal, representative of the intensity of the emission in the primary narrow wavelength band is provided to a microprocessor or other means for determining the proportion of the element corresponding to the primary band in the gas. The means for determining may include retrieval means for retrieving a stored predetermined proportion of the component in the gas corresponding to the signal representative of the intensity of the emission in the primary band. Alternatively, means may be provided for calculating the proportion of the component in the gas. The means for determining may be temperature and/or pressure dependent. An oscilloscope, computer read-out or other means may be provided for indicating the intensity of the emission in the primary bands of interest and therefore the proportion of the corresponding elements in the gas. An audio or visual alarm may also be provided for indicating the presence of at least a predetermined proportion of each element in the gas. Such a feature is particularly important for the monitoring of elements which identify a gas sample as poisonous.

In certain embodiments, fiber optics or other conduit means may be provided for conducting the radiation emitted by the spark discharge from the spark chamber to the means for detecting.

Figure 1:
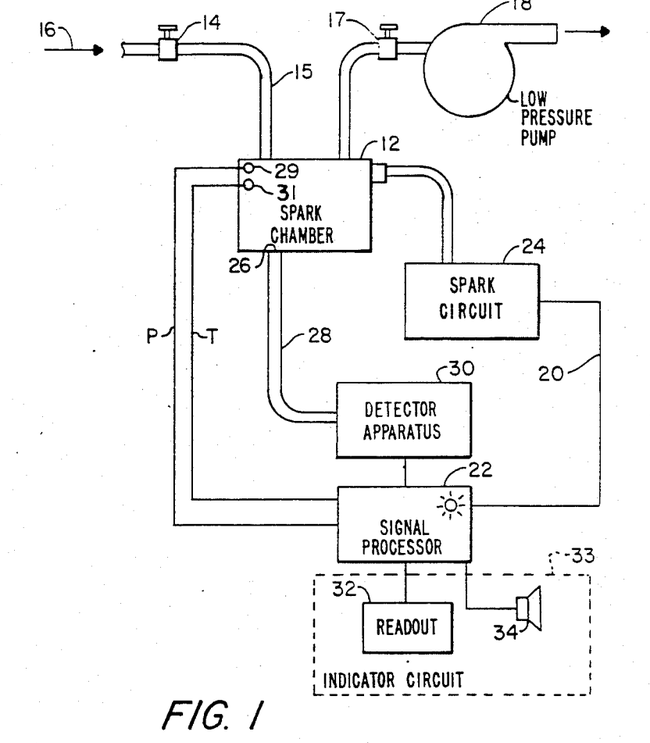
FIG. 1 is a schematic diagram of a trace element detection system according to this invention.

There is shown in FIG. 1 a spark discharge trace element detection system 10 including a spark chamber 12. A valve 14 is opened to introduce sample gas 16 through conduit 15 into chamber 12. Valve 14 and a similar valve 17 are used to maintain a predetermined pressure and flow rate in chamber 12. A low-pressure pump 18 maintains the pressure within chamber 12 below one atmosphere and preferably at at least 0.1 atmosphere. It should be noted, however, that prior to entering chamber 12 gas 16 may be maintained at any pressure level, including atmospheric or higher. In response to timed signals over line 20 from signal processor 22, spark circuit 24 applies a voltage across a pair of spaced-apart electrodes, not shown in FIG. 1 but described in connection with FIG. 2, within the spark chamber which generates sparks in chamber 12. This creates a plasma which emits intense continuous background radiation. Radiation is also emitted by the trace elements to be detected in the sample gas within the spark chamber. This emitted radiation passes through a window 26 in chamber 12 and is directed through an optical fiber 28 to a detector apparatus 30. The detector apparatus measures the intensity of the emitted radiation in one or more selected narrow wavelength bands as described more fully below. Signals representative of these intensities are then provided to a signal processor 22 where they are processed along with signals representative of the temperature T and pressure P monitored by sensors 31 and 29 within chamber 12 to identify the constituent trace elements and their proportions present in the sample gas. The trace element concentrations may be indicated, for example, by a read-out 32 of indicator circuit 33 and when the concentration of any particular element exceeds a predetermined safe level an alarm 34 may be sounded.

Figure 2:
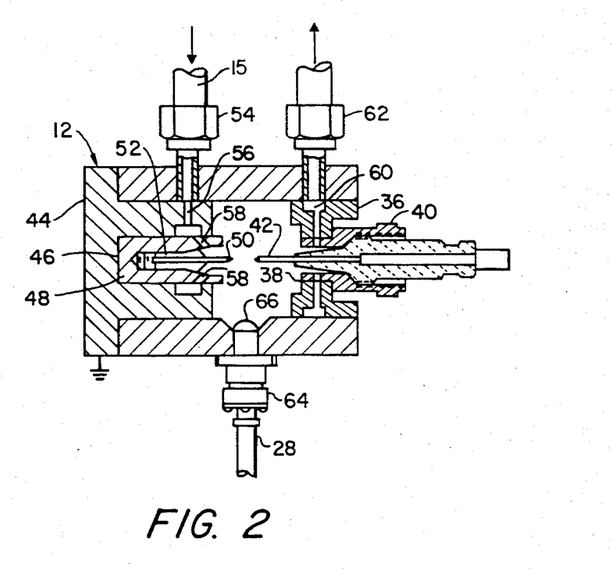
FIG. 2 is a cross-sectional view of the spark discharge chamber of FIG. 1.

Spark chamber 12, FIG. 2, includes a first manifold 36 having a threaded opening 38 for receiving the threaded collar 40 of a high-voltage electrode 42. Electrode 42 is itself connected in a conventional manner to a high-voltage discharge supply of spark circuit 24, FIG. 1. Chamber 12 also includes a second manifold 44 which has a central recess 46 for receiving a third manifold 48. A ground electrode 50 is mounted by a collet 52 within manifold 48 and is spaced apart from electrode 42 at a distance which enables pulsed sparks to be produced across electrodes 42 and 50 when high voltage is applied to electrode 42. Manifolds 36 and 44 serve as ground connections for the mounted electrodes 42 and 50.

Sample gas is introduced into chamber 12 through a VCR fitting 54 which is connected to conduit 15, FIG. 1. Fitting 54 communicates with a channel 56 that extends through manifold 44 and peripherally surrounds manifold 48. An orifice 58 interconnects channel 56 with the interior of chamber 12. As a result, sample gas is introduced through channel 56 and orifice 58 so that it flows into the chamber generally parallel past electrodes 50 and 42. Low-pressure pump 18, FIG. 1, removes sample gas from the interior of chamber 12 through a channel 60 in manifold 36 and a VCR fitting 62 which is attached to chamber 12 and communicates with channel 60. The pump operates at a level required to maintain the pressure of the sample gas in chamber 12 at subatmospheric levels.

Optical fiber 28 is mounted by a collar 64 to chamber 12 and includes a collecting lens 66 mounted at the end of the optical fiber within chamber 12. The radiation emitted by the spark across electrodes 42 and 50 is collected by lens 66 and transmitted through optical fiber 28 to detector apparatus 30, FIG. 3. Therein, the emitted radiation 68 is collimated by a lens 70. The collimated light is directed onto a dispersive grating 72 which separates the spark discharge emission into its constituent wavelengths. The separated light 74 strikes a detector array 76 which includes individual detectors 78, 80 and 82 for detecting the intensity of primary narrow wavelength bands corresponding to trace elements being monitored in the sample gas.

Figure 3:
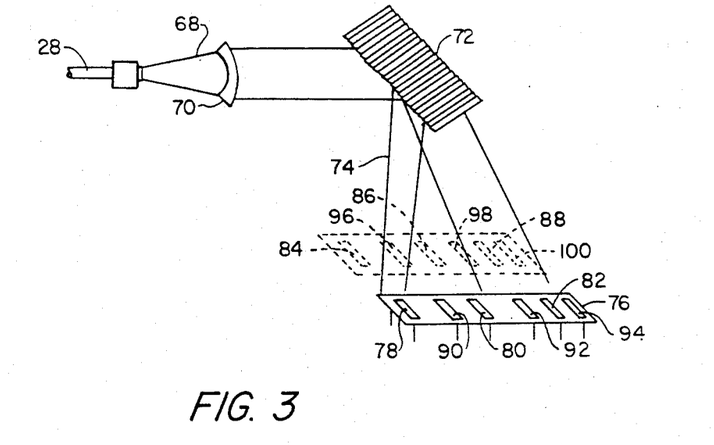
FIG. 3 is a simplified axonometric view of elements contained within the detector apparatus of FIG. 1.

To distinguish the atomic lines of interest from the background continuum radiation, interference filters or other bandpass filters 84, 86 and 88 are disposed in front of the respective detectors. Typically, each filter and each detector selects and detects a single associated wavelength band. For example, if detection of fluorine, chlorine and sulfur is desired, filter 84 and detector 78 may be selected to detect a wavelength band which includes 6856 Angstroms (fluorine); filter 86 and detector 80 may be selected to detect a band which includes 8375 Angstroms (chlorine); and filter 88 and detector 82 may be selected to detect the band which includes 9212 Angstroms (sulfur).

To compensate for variations in the spark intensity over successive spark emissions additional detectors 90, 92 and 94 and associated filters 96, 98 and 100 may be provided for detecting the intensity of the spark discharge in one or more secondary wavelength bands which do not correspond to the respective elements to be detected within the gas sample. For example, detector 90 senses a secondary wavelength band not emitted by fluorine; detector 92 senses a wavelength band not emitted by chlorine; and detector 94 senses a wavelength band not emitted by sulfur.

Figure 4:
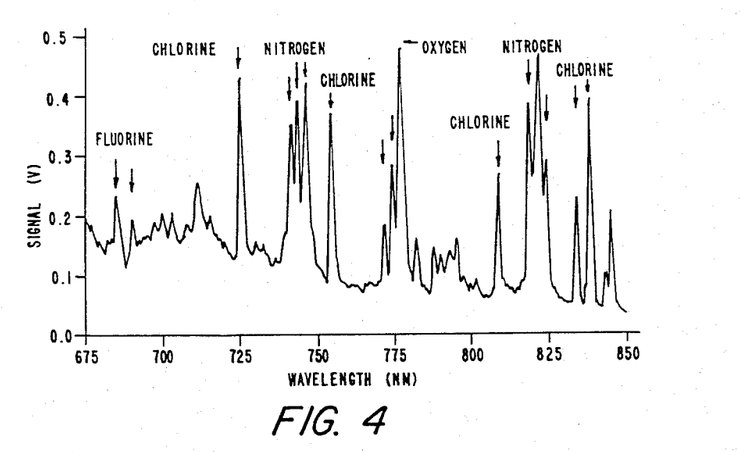
FIG. 4 shows a portion of the emission spectrum of an atmospheric sample containing freon.

The detectors provide to signal processor 22, FIG. 1, intensity signals whose strength is proportional to the intensity of the radiation emitted in the respective wavelength bands. The near infrared spectrum (i.e., 6750–8500 Angstroms) of a sample gas of 5% Freon-12 in room air at a pressure of 0.170 atmospheres is shown in FIG. 4. Voltage peaks indicate the wavelength bands of most intense emission and hence serve to identify the constituent elements in the sample gas. The nitrogen and oxygen peaks are representative of the room air in the gas sample.

Figure 5:
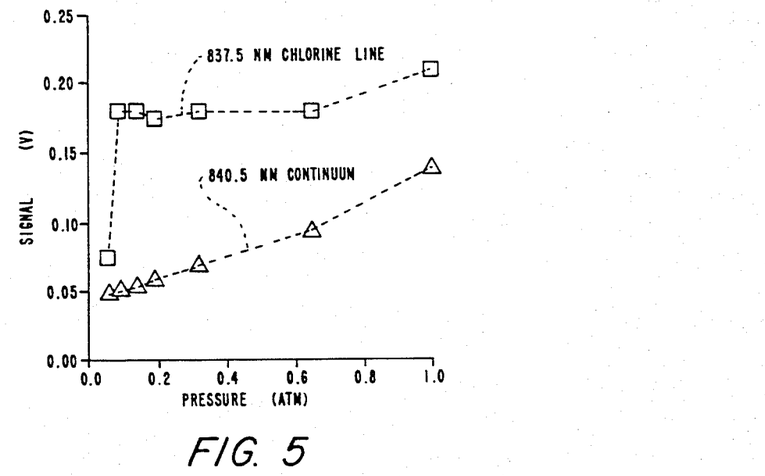
FIG. 5 illustrates curves representing the signal strength of a detected chlorine emission line versus gas pressure and the signal strength of interfering background emission versus gas pressure.

In order to detect the presence and concentration of the constituent trace element chlorine a representative primary wavelength band, for example the band centered about 8375 Angstroms, is selected. As shown in FIG. 5 the intensity of the signal produced by the emission in that band remains virtually constant as the pressure is reduced from 1 to 0.1 atmosphere whereas the intensity of the continuum background signal drops off sharply. Accordingly, as indicated in FIG. 4 the chlorine line at 8375 Angstroms is sharp and distinguishable from the surrounding background emission.

Figure 6:
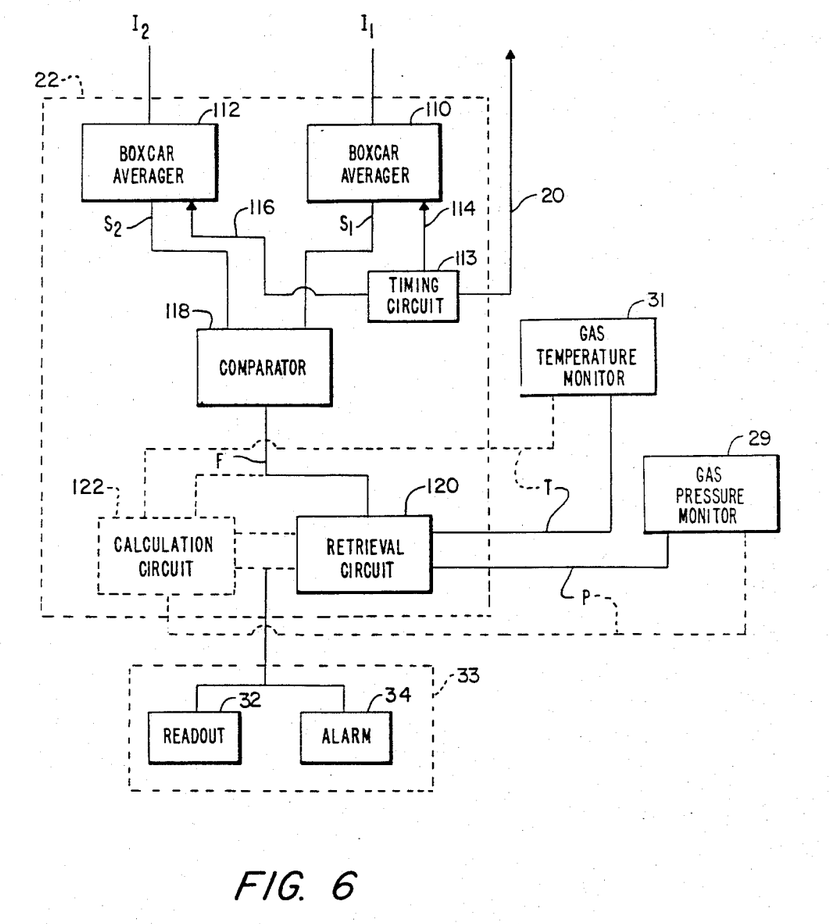
FIG. 6 is a detailed schematic diagram of the signal processor and indicator circuit of FIG. 1.
Figure 7:
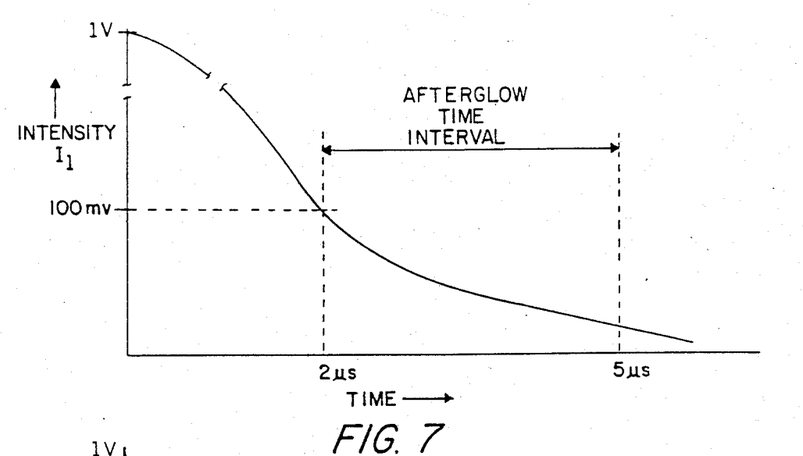
FIG. 7 is a curve illustrating variation in the intensity over time of the emitted radiation in a selected primary wavelength band corresponding to the component being detected.

The intensity signals of the primary and secondary bands for each monitored trace element are processed by a respective signal processor 22 as follows. As indicated in FIG. 6, a signal $I_1$ representative of the intensity of the detected radiation in the primary selected band and signal $I_2$ representative of the intensity of the detected radiation in the secondary selected band are provided to processor 22. In particular, signals $I_1$ and $I_2$ are delivered to respective boxcar averagers 110 and 112. As shown in FIG. 7, the intensity of signal $I_1$ immediately after each spark initiation is approximately one volt. At that time the signal is due mainly to the background intensity of the spark plasma. The signal strength subsequently drops to approximately 100 millivolts at the beginning of the afterglow interval (e.g., at about 2 microseconds following spark initiation). By this time the effects of the background emission have largely subsided. During the afterglow period of approximately 2–5 microseconds following discharge the background intensity has subsided sufficiently so that the emission spectra of the trace element being detected are evident and distinguishable from the background radiation. Because the gas sample is maintained at subatmospheric pressure distinction between the trace element's emission spectra and the background spectrum is even more pronounced. Timing circuit 113, FIG. 6, which provides signals at predetermined times over line 20 to activate spark circuit 24, FIG. 1, also provides a timed signal at the beginning of the afterglow period, e.g., 2 microseconds, over line 114 to boxcar averager 110. This causes the boxcar averager to integrate the intensity of signal $I_1$ during the afterglow period. At the end of the afterglow period, timing circuit 113 instructs boxcar averager 110 to stop integration. The boxcar averager averages a number of successive integrated intensity signals to compensate for variations in the intensity of the spark itself over successive discharges. It then provides a signal $S_1$ which is representative of (e.g., a function of) the pulse-averaged intensity of the emission in the first wavelength band.

Figure 8:
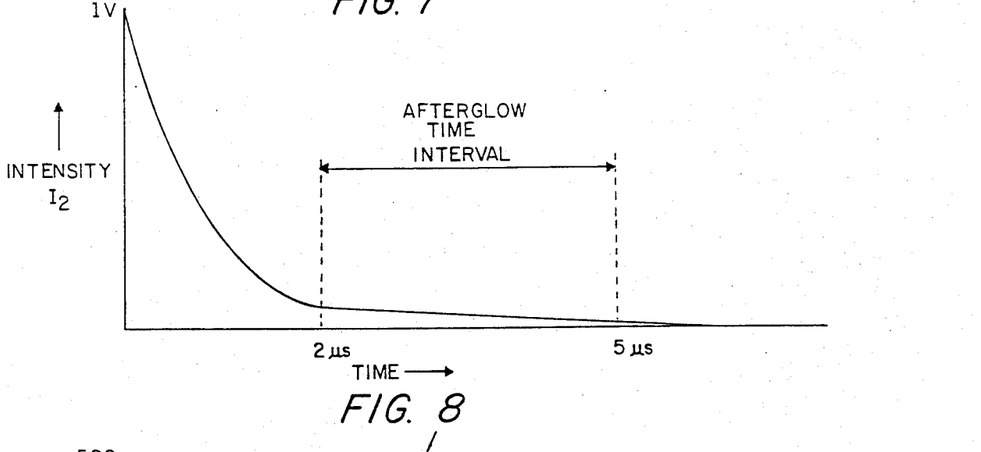
FIG. 8 is a curve illustrating variation in the intensity over time of the emitted radiation in a secondary narrow wavelength band not corresponding to the component being detected.

The time evolution of signal $I_2$ including a wavelength of 8405 Angstroms is shown in FIG. 8. Because the characteristic emission line which corresponds to the subject element is absent, the intensity in the secondary band drops off rapidly. At 2 microseconds after discharge, timing circuit 113 provides a signal over line 116 to second boxcar averager 112, which is operated during the afterglow time interval to integrate signal $I_2$. The integrated intensity signal is then averaged by boxcar averager 112 to yield a signal $S_2$. Instead of a single distinct timing circuit, separate timing circuits may be provided integrally with each of the boxcar averagers.

Signals $S_1$ and $S_2$, FIG. 6, are delivered to a comparator 118 where they are divided, subtracted or otherwise combined or compared to provide signal F which is representative of the integrated intensity of the radiation in the first band compensated for variations, e.g., false readings, caused by, for example, contaminants, dirty optics, or variations in background radiation. That signal is provided to a retrieval circuit 120 where the proportion of the trace element in the sample is retrieved from calibration curves stored in the memory of the circuit. Alternatively, the proportion of the trace element in the sample gas may be determined by entering signal F into a calculation circuit 122. In either embodiment gas pressure sensor 29 monitors the pressure in the sample and temperature monitor 31 senses the temperature of the sample. Retrieval circuit 120 or calculation circuit 122 responds to the gas pressure and temperature measurements to determine the proportion of for example of Freon in air or water in helium at the sensed pressure and temperature. The determined water proportion is indicated on a read-out 32 of indicator circuit 33. If the proportion reaches a desirably high level an alarm 34 is activated. In alternative embodiments a single secondary wavelength band may be used with a number of primary wavelength bands. Typically in such cases the intensity output of each primary wavelength is provided to a respective boxcar averager or other integrator before comparison with the reference signal.

Figure 9:
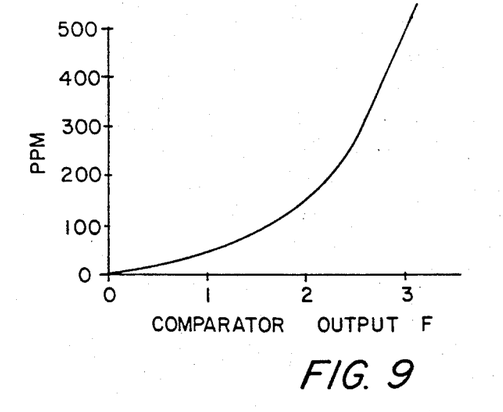
FIG. 9 is a curve illustrating the comparator output F versus the proportion of trace element in the gas sample.

A curve which may be used by circuit 120 for determining stored concentration values for a gas sample for a chlorine containing compound such as Freon, for example, is shown in FIG. 9. Values along the x axis represent the normalized signal F provided to the retrieval circuit. Values along the y axis indicate the proportion of the trace element in parts per million. The calibrated curve is compiled by employing gas samples having known trace element concentrations and predetermined temperatures and pressures and measuring the values F for such samples.

Figure 10A:
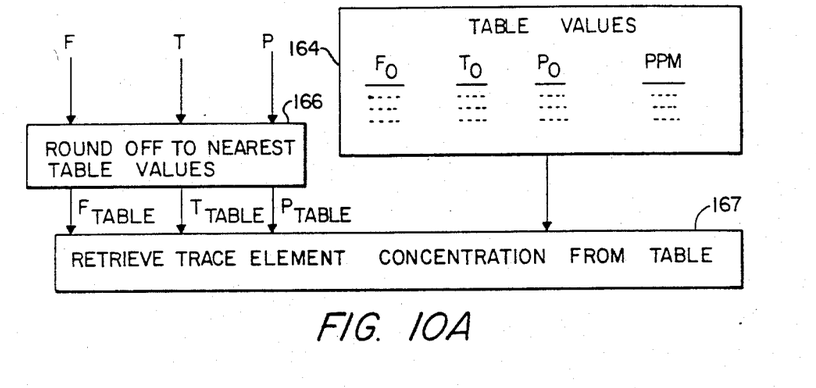
FIG. 10A is a flow chart for retrieving from a table the proportion of trace elements in the gas sample.
Figure 10B:
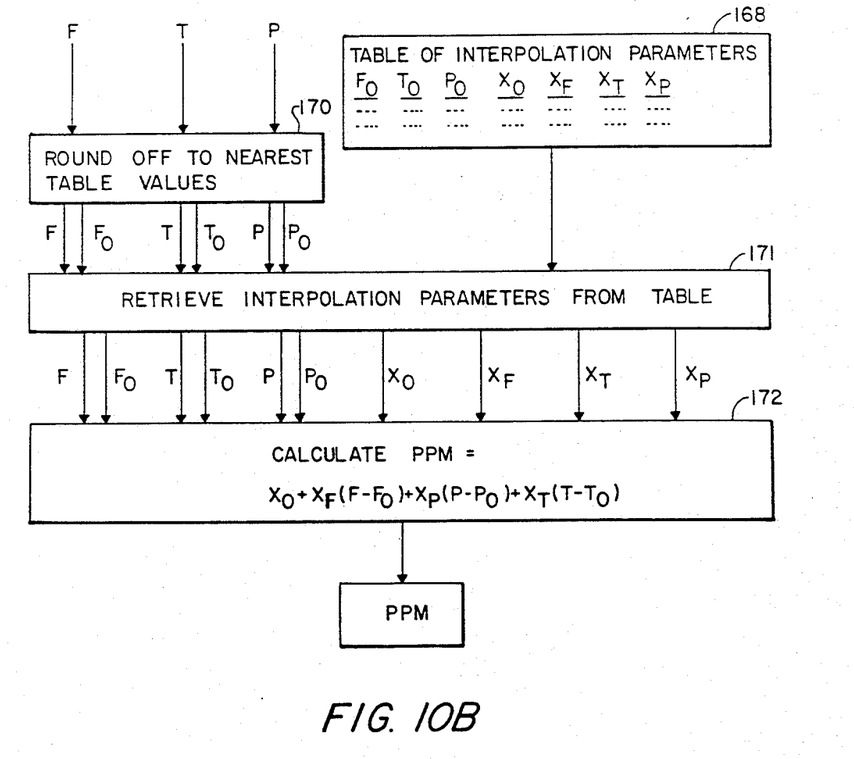
FIG. 10B is a flow chart for interpolating the proportion of trace element in the gas sample.

Logic which may be used to resolve the concentration of trace element in a gas sample is shown in FIGS. 10A and 10B. In FIG. 10A predetermined values of signal $F_0$, temperature $T_0$ and pressure $P_0$ and corresponding values of trace element concentration (in ppm) are provided in a table 164. The measured values F, T and P are rounded off to the nearest table values $F_0$, $T_0$ and $P_0$ and the trace element concentration corresponding to the three values is retrieved, 167, from table 164.

Alternatively, interpolation may be employed as shown in FIG. 10B. Table 168 includes various known values for the integrated comparison signal $F_0$, the temperature $T_0$ and pressure $P_0$ as well as corresponding values of trace element concentration $X_0$ and interpolation parameters $X_F$, $X_T$ and $X_P$ for the $F_0$, $T_0$ and $P_0$ values. The measured values F, T and P are rounded off, 170, and paired with corresponding table values $F_0$, $T_0$ and $P_0$. The corresponding values in table 168 are retrieved, 171, to acquire the appropriate trace element concentration $X_0$ and interpolation parameters $X_F$, $X_T$ and $X_P$ for $F_0$, $T_0$ and $P_0$. Trace element concentration for the measured sample is then resolved by interpolation and in particular by calculating, step 172, the expression:

$$X_0 + X_F(F - F_0) + X_P(P - P_0) + X_T(T - T_0).$$

Figure 11:
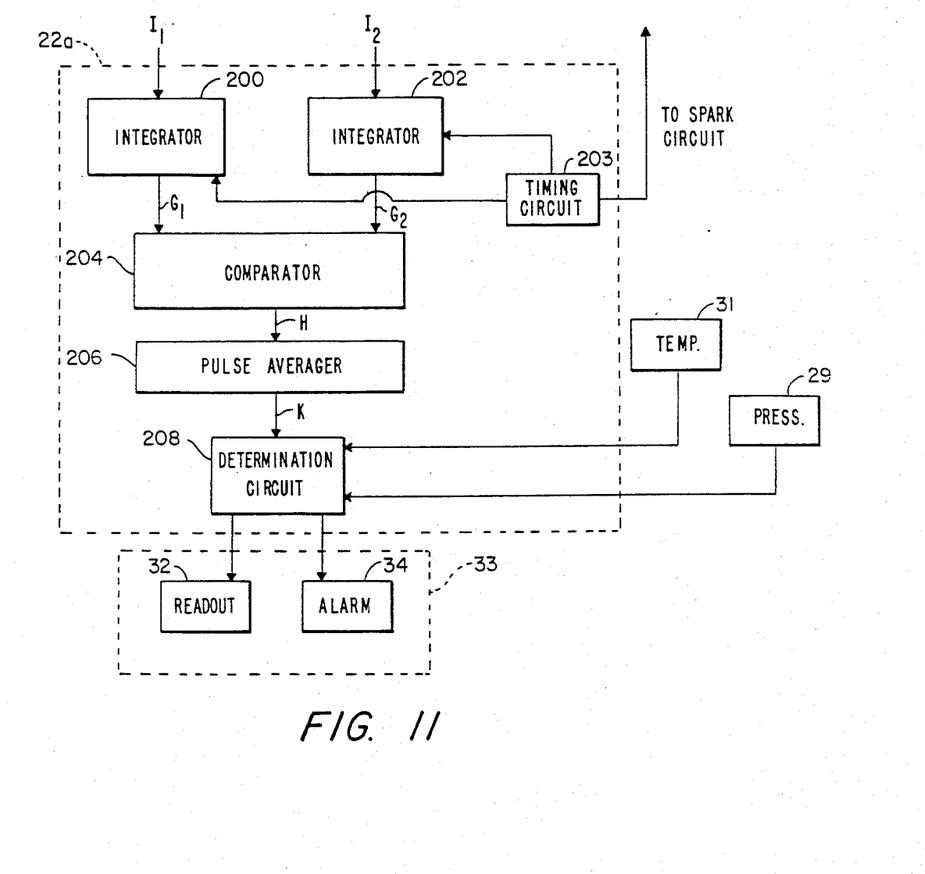
FIG. 11 is a detailed schematic diagram of an alternative signal processor according to this invention.

In a preferred embodiment, FIG. 11, signal processor 22a includes a pair of integrators 200, 202 operated at timed intervals by timing circuit 203 to integrate the respective intensity signals $I_1$ and $I_2$ during the afterglow time interval and provide integrated signals $G_1$ and $G_2$ to comparator 204. There the signals are compared by dividing or subtracting them or otherwise processing them to provide a compensated signal which is representative of the compensated intensity of the radiation of the first band. Pulsed signal H is then averaged over many sparks in pulse averager 206 which may be a low pass filter and which provides a smoothed signal K to a determination circuit 208. Circuit 208 typically includes either a retrieval or calculation circuit as previously described which responds to the integrated, averaged, compensated signal as well as to pressure and temperature signals from pressure sensor 29 and temperature sensor 31 for resolving the trace element concentration, e.g., the concentration of chlorine, arsenic, carbon or other trace element monitored in the gas sample. Read-out 32 and alarm 34 of indicator circuit 33 again provide appropriate indications of the proportion of trace element in the sample.

Although specific features of the invention are shown in some drawings and not others, this is for convenience only as each feature may be combined with any or all of the other features in accordance with the invention.

Other embodiments will occur to those skilled in the art and are within the following claims.

What is claimed is:

1. A spark discharge trace element detection system comprising:
   a spark chamber including a pair of electrodes for receiving a sample of gas to be analyzed at no greater than atmospheric pressure;
   means for regulating the gas pressure in said spark chamber to remain no greater than one atmosphere;
   means for providing a voltage across said electrodes for generating a spark in said gas sample;
   means for detecting the intensity of radiation emitted from the spark discharge in at least one primary selected narrow band of the radiation emitted from the spark discharge in said gas sample, each primary band corresponding to an element to be detected in the gas;
   means for integrating, during the afterglow time interval of the spark emission, the intensity of the emission in each detected primary band; and
   means responsive to a signal representative of the integrated intensity of the emission in each selected primary band for determining the concentration of the corresponding element in the gas.

2. The detection system of claim 1 further including means for compensating the intensity of the emission in a said primary wavelength band for variations not due to variations in the proportion of the element being detected in the gas.

3. The detection system of claim 2 in which said means for compensating includes means for averaging a signal representative of the intensity of the emission in the primary band over a plurality of spark discharge cycles.

4. The detection system of claim 3 in which said means for integrating and said means for averaging a signal representative of the intensity of the emission in the first primary band are included in a boxcar averager.

5. The detection system of claim 2 in which said means for compensating includes means for detecting the radiation emitted from the spark discharge in the gas in a secondary selected narrow band of the emitted radiation which does not correspond to an element to be detected in the gas, and means for combining a signal representative of the intensity of the emission in the primary band with a signal representative of the intensity in the secondary band.

6. The detection system of claim 5 in which said means for compensating further includes means for integrating, during the afterglow time interval of the spark emission, the intensity of the radiation in the secondary selected band.

7. The detection system of claim 6 in which said means for compensating further includes first means, responsive to said means for integrating the intensity of emission in the primary band, for averaging over a plurality of spark discharge cycles the integrated intensity of emission in the primary band and second means, responsive to said means for integrating the intensity of emission in the secondary band, for averaging over a plurality of spark discharge cycles the integrated intensity of emission in the secondary band.

8. The detection system of claim 7 in which said means for integrating the intensity and means for averaging the integrated intensity in the primary selected band are included in a boxcar averager.

9. The detection system of claim 7 in which said means for integrating the intensity and means for averaging the integrated intensity in the secondary selected band are included in a boxcar averager.

10. The detection system of claim 7 in which said means for combining includes means, responsive to said first and second means for averaging, for comparing the averaged integrated intensity of the emitted radiation in the primary band and the averaged integrated intensity of the emitted radiation in the secondary band and providing to said means for determining an output representative of the averaged integrated intensity of the emission in the primary band.

11. The detection system of claim 6 in which said means for combining includes mean for comparing the integrated intensity of the emission in the primary band and the integrated intensity of the emission in the secondary band.

12. The detection system of claim 11 in which said means for combining further includes means responsive to said means for comparing for averaging over a plurality of spark discharge cycles the output from said means for comparing and providing an averaged output to said means for determining.

13. The detection system of claim 5 in which said means for detecting the emitted radiation in a secondary selected band includes filter means for selecting said secondary band.

14. The detection system of claim 13 in which said filter means includes an interference filter.

15. The detection system of claim 1 further including means for sensing the pressure of said gas to be analyzed, said means for determining being further responsive to said means for sensing the pressure for determining the proportion of the element in the gas at the sensed pressure.

16. The detection system of claim 1 further including means for sensing the temperature of said gas to be analyzed, said means for determining being further responsive to said means for sensing the temperature for determining the proportion of the element in the gas at the sensed temperature.

17. The detection system of claim 1 further including conduit means for conducting radiation emitted by said spark discharge from said chamber to said means for detecting.

18. The detection system of claim 17 in which said conduit means includes fiber optics.

19. The detection system of claim 1 in which said means for determining includes means for calculating the proportion of the element in the gas.

20. The detection system of claim 1 in which said means for determining includes means for retrieving a stored predetermined proportion of the element in the gas corresponding to a signal representative of the integrated intensity of the emission in the primary band.

21. The detection system of claim 1 in which said means for detecting the emitted radiation in at least one primary band includes filter means for selecting said primary narrow band.

22. The detection system of claim 21 in which said filter means includes at least one interference filter, each said filter selecting an associated primary band.

23. The detection system of claim 1 in which said means for detecting includes at least one detector, each detecting a single associated narrow band of radiation.

24. The detection system of claim 1 further including means, responsive to said means for determining, for indicating the proportion of the element in the gas.

25. The detection system of claim 1 further including alarm means, responsive to said means for determining, for indicating the presence of at least a predetermined proportion of the element in the gas.

26. The detection system of claim 1 in which said gas to be analyzed has a pressure of at least one-tenth atmosphere in said chamber.

27. The detection system of claim 1 in which said electrodes are spaced apart between 1 mm and 3 mm.

28. The detection system of claim 1 in which the voltage applied across said electrodes is at most fifty kilovolts.

29. The detection system of claim 1 in which said means for determining includes a microprocessor.

30. The detection system of claim 1 in which a said primary band includes at least one wavelength from the group including 2169, 2288, 2479, 2533, 6856, 8375, and 9212 Angstroms.

31. A spark discharge trace element detection system comprising:
   a spark chamber including a pair of electrodes for receiving a sample of gas to be analyzed at no greater than atmospheric pressure;
   means for regulating the gas pressure in said spark chamber to remain no greater than one atmosphere;
   means for providing a voltage across said electrodes for generating a spark in said gas sample;
   means for separating radiation emitted from the spark discharge into its constituent wavelengths;
   means for detecting the intensity of the emitted radiation in at least one primary selected narrow band of said constituent wavelengths, each primary band corresponding to a respective element to be detected in the gas;
   means for integrating, during the afterglow time interval of the spark emission, the intensity of the emission in each detected primary wavelength band; and
   means responsive to a signal representative of the integrated intensity of the emission in each selected primary wavelength band for determining the concentration of the corresponding element in the gas.

the spark discharge in at least one primary selected narrow band of the radiation emitted from the spark discharge in said gas sample, each primary band corresponding to an element to be detected in the gas;

means for integrating, during the afterglow time interval of the spark emission, the intensity of the emission in each detected primary band;

means for sensing the pressure of said gas being analyzed;

means for sensing the temperature of said gas being analyzed; and means responsive to said means for sensing the temperature and pressure of said gas being analyzed and to a signal representative of the integrated intensity of the emission in each selected primary band, for determining the proportion of the corresponding element in the gas at the sensed pressure and temperature.

32. A spark discharge trace element detection system comprising:

a spark chamber including a pair of electrodes for receiving a sample of gas to be analyzed at no greater than atmospheric pressure;

means for regulating the gas pressure in said spark chamber to remain no greater than one atmosphere;

means for providing a voltage across said electrodes for generating a spark in said gas sample;

means for detecting the intensity of radiation emitted from the spark discharge in at least one primary selected narrow band of the radiation emitted from the spark discharge in said gas sample, each primary band corresponding to an element to be detected in the gas;

means for integrating, during the afterglow time interval of the spark emission, the intensity of the emission in each detected primary band;

means for sensing the pressure of said gas being analyzed;

means for sensing the temperatue of said gas being analyzed; and means, responsive to said means for sensing the temperature and pressure of said gas being analyzed and to a signal representative of the integrated intensity of the emission in each selected primary band, for determining the proportion of the corresponding element in the gas at the sensed pressure and temperature.

* * * * *